(12) United States Patent
Rizo et al.

(10) Patent No.: US 6,249,568 B1
(45) Date of Patent: Jun. 19, 2001

(54) PROCESS FOR IMPROVING A SIGNAL/NOISE RATIO OF THE IMAGE OF A MOVING OBJECT

(75) Inventors: Philippe Rizo, La Tronche; Roland Sauze, Gnenoble, both of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/335,834

(22) Filed: Jun. 18, 1999

(30) Foreign Application Priority Data

Jun. 19, 1998 (FR) .................................... 98 07759

(51) Int. Cl.[7] ....................................... A61B 6/02
(52) U.S. Cl. ............................ 378/98.12; 378/23
(58) Field of Search .................... 378/98.12, 21, 378/22, 23, 24, 25, 26

(56) References Cited

U.S. PATENT DOCUMENTS 5,668,844 * 9/1997 Webber .................................. 378/23
5,974,108 * 10/1999 Taguchi et al. ........................ 378/4
6,081,577 * 6/2000 Webber .................................. 378/23

FOREIGN PATENT DOCUMENTS 0 814 430 A1    12/1997  (EP) .

OTHER PUBLICATIONS

Özkan, et al., "Adaptive Motion–Compensated Filtering of Noisy Image Sequences," IEEE Transactions on Circuits and Systems for Video Technology, No. 4, Aug. 1993, pp. 277–290.

* cited by examiner

Primary Examiner—Robert H. Kim
Assistant Examiner—Drew A. Dunn
(74) Attorney, Agent, or Firm—Anderson, Kill & Olick P.C.

(57) ABSTRACT

The invention relates to a radiography process for use with an object moving between a source and a detector involving a determination of a plane called the object projection plane and the production of radiographic images of the object while it is moving using the source, the detector and the combination of the various contributions of projections of the projection plane in the series of radiographic images.

12 Claims, 4 Drawing Sheets

PROCESS FOR IMPROVING A SIGNAL/ NOISE RATIO OF THE IMAGE OF A MOVING OBJECT

TECHNICAL DOMAIN AND PRIOR ART

The invention described relates to the problem of radioscopy processing of moving objects.

In general, pose times for radioscopy of moving objects are short. This results in very noisy images, since only a small number of photons are detected while taking the X-ray. Two techniques are commonly applied to overcome this problem.

When the object moves slowly, the simplest technique consists of summating a small number of successive radiographs (sliding total), assuming that these images are identical. In this case a loss of geometric resolution is accepted in return for a reduction of noise on the images. This function is usually provided on most real time image processing systems. If n photons arrive per pixel on the detector for each radiograph, the signal to noise ratio of the radiograph will be $\sqrt{n}$. If m successive images are summated to generate an image with less noise, the signal/noise ratio of this image will be $\sqrt{n \cdot m}$. However, the geometric resolution is lower. If the object moves by $\Delta x$ between two successive radiographs, the order of magnitude of the system resolution will be $m \cdot \Delta X$.

Another technique for quickly moving objects consists of summating a small number of successive radiographs by shifting them to take account of the movement of the object. This technique is commonly called TDI (Transfers Delay Integration) in CCD technology. In instruments, TDI is usually used in the sensor. In the case of CCD sensors, charges in the detector move at the same time as image points. This means that the summation can be done by analog means, limiting firstly the number of data to be transferred, and secondly the number of operations to be executed on the CPU.

This technique is limited to a small number of contributions since projections of the various structures in the object do not move at the same speed on the screen, depending on their arrangement within the depth of the object. If a large number of successive images is summated, the resulting image will represent a single plane of the object. Two configurations can be considered to illustrate this problem.

Firstly, in the case of an object that is thin compared with the source-detector distance, the position of a structure within the depth of the object will have very little influence on the position of the projection. Consequently, the TDI operation can be applied to the entire sensor, in other words to the number of images corresponding to the presence of the structure searched for on the image. The TDI is the reference method in this configuration.

In the case of an object with a significant thickness with respect to the source-detector distance, the position of the projection of a structure moves a great deal as a function of the depth component of its position. Therefore, the TDI cannot be easily applied. The TDI will tend to produce a sharp image of the plane corresponding to the offset between superposed images, and a blurred image of other parts of the object. In particular, specific processing had to be developed for this configuration, and this processing is the subject of this invention.

In the case of a quickly moving object, the object moves a long way on all images to be combined. Typically, in an application for the inspection of rocket propulsion units, the number of radiographs that may be used in a sliding total is of the order of 6. The geometric resolution of the resulting image degrades very quickly for larger numbers. In the same manner, the use of TDI is limited to about 20 radiographs in which only the central detector area is used.

DESCRIPTION OF THE INVENTION

One purpose of the invention is to supply a radiographic image of a thick moving object which would combine a large number of successive images of this object during its displacement.

The proposed method consists of improving the signal to noise ratio in the radiograph, concomitant with a slight deterioration in the geometric resolution of the radiograph. Depending on the processing used, an image is generated which will be as similar as possible to the radiograph that would be obtained with the source at infinity. This is the radiograph that would be obtained if each ray arrived at the detector along a plane perpendicular to the detector called the projection plane. The proposed method uses the information contained in the detector area corresponding to the projection of the projection plane during its displacement.

The proposed method provides a means of combining a large number of radiographic images in order to limit noise on images while limiting the loss of geometric resolution. The other advantage of this method is that it can be used on the same software architecture as tomosynthesis. Consequently, this method may be used in real time in radioscopy.

The first purpose of the invention is a radiography process for use with a moving object between a source and a detector, comprising:

determination of a plane (P), called the object projection plane, such that the radiographic image of this plane is a line, for one of the positions of the moving object, the production of radiographic images of the object while it is moving, using the source and the detector, the combination of the various contributions of projections of the projection plane in the series of radiographic images obtained.

The combination step may be a step in which the values corresponding to the projection of the projection plane are summated.

According to one embodiment, the object moves in translation along a direction (D) and has a thickness l along the direction of the projection plane, the number of combined pixels to generate one pixel in the resulting image being equal to:

$$N_{ps} = \sum_{i=1}^{i=m} \left( \frac{l \cdot \Delta x \cdot m}{(FG + l)} \times \frac{FGd}{FG} \times \frac{1}{P} + 1 \right)$$

where p is the size of a pixel, and where FG and FGd represent the distance between the source and the object, and the distance between the source and the detector respectively, and where m is the number of successive positions of the object separated by a distance $\Delta x$ for which an image is created.

The object may also move along a circular path, the projection plane being a radial plane from the object.

A correspondence table may be built up associating each pixel in the radiographic image with a pixel on the projection line from the projection plane.

Thus, a table Tab(k, Ie, Je)=Js can be defined which associates pixel (Ie, Je) in image N+k, where k is a positive or negative integer, with pixel Js in the projection from the projection plane.

Another purpose of the invention is a process for taking a radiograph of an object moving between a source and a detector, comprising:

determination of an area $S_0$ for a given position of the object, this area being projected onto the detector along a curve $(C_1)$, its projection taking place based on an area $S_p$ in its other positions, production of radiographic images of the object as it moves, using the source and the detector, processing of the projection along $(C_1)$, this processing comprising the following steps:

a) elementary breakdown of the area $S_0$, firstly along lines 1 along the direction of the radiation from the source to the detector (called radiation attenuation lines) and secondly along lines in a direction different from the direction of lines 1, each point on the meshed area being identified by its coordinates $(I_e, J_e)$, b) for each position k of the object, calculation of the position $(I_d, J_d)$, in $S_p$, of the projection onto the detector of each point identified by its coordinates $(i_e, J_e)$, the value of the measurement in $(I_d, J_d)$ being $f(I_d, J_d)$ on $S_p$, c) calculation of the projection of $S_0$ on $C_1$ which is a function of $I_d$, for all positions of the area $S_0$ while the object is moving, starting from the different positions k of the area, and definition of a function:

$$\sum_{k}\sum_{Jd} fk(I_d, J_d) = projIe,$$

d) movement of the object, identifying the new position of $S_0$ in the object which had moved by one elementary position, then return to step c), e) line by line construction of the radiograph, each line being stored.

BRIEF DESCRIPTION OF THE FIGURES

In any case, the characteristics and advantages of the invention will become clearer after reading the following description which relates to example embodiments given for explanatory purposes and in no way restrictive, with reference to the attached drawings in which.

DETAILED DESCRIPTION OF EMBODIMENTS OF THE INVENTION

Figure 1:
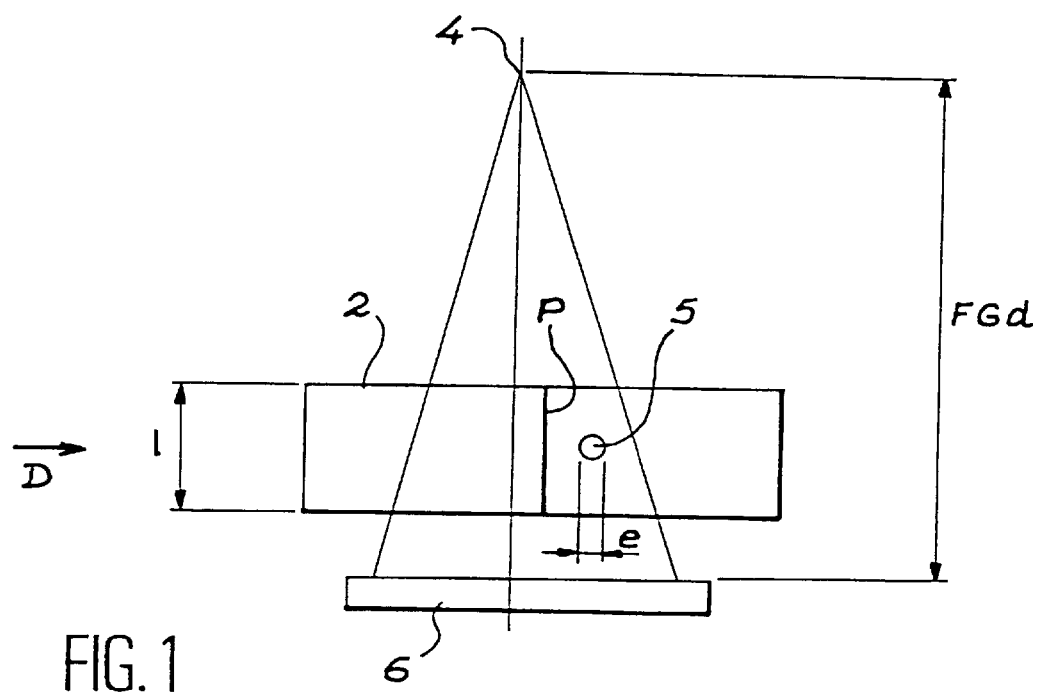
FIGS. 1 and 2 illustrate one embodiment of the invention.

FIG. 1 illustrates a first embodiment of the invention. It is assumed that there is a rectangular object 2 with thickness l, translating between a source 4 and a detector 6. The projection plane P is assumed to be a plane perpendicular to the direction D of displacement J of the object.

Figure 2:
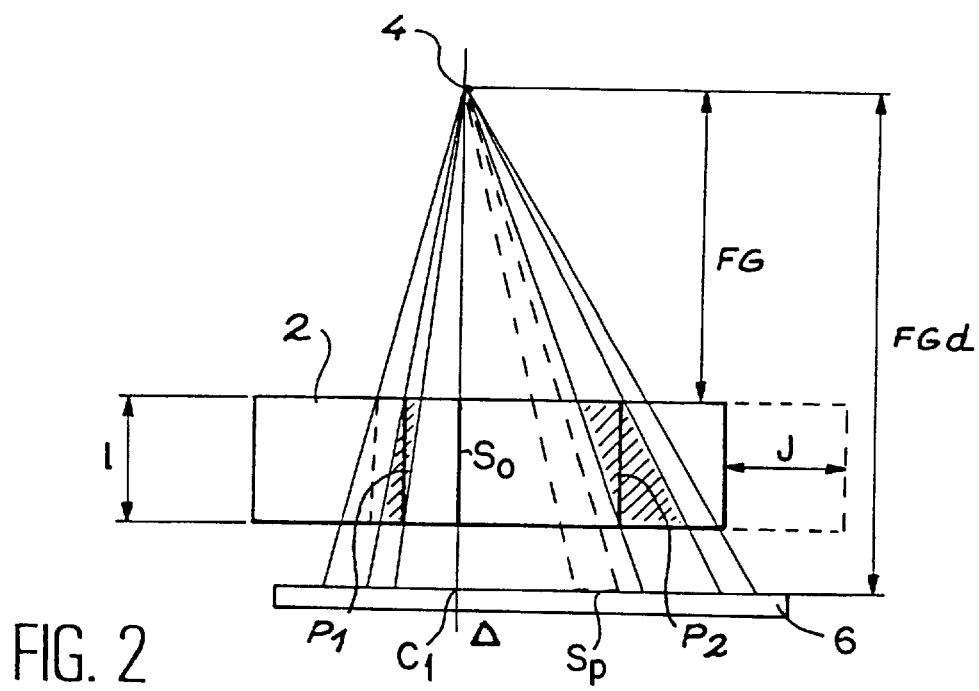

FIG. 2 represents two different positions $P_1$ and $P_2$ of the projection plane during the movement of object 2.

If it is assumed that the attenuation of the object is equal to 1 and the attenuation of a defect 5 with diameter e is equal to 2, the contrast of the defect on the radiography (in density) is equal to $$\frac{e+l}{l},$$

with a signal/noise ratio of $\sqrt{n}$, if n is the number of photons that are detected after passing through the object.

In order to improve the signal/noise ratio of the final radiographic image, the various contributions of the projections of the projection plane in the series of images, are combined. In fact, the values corresponding to the projection of the projection plane are summated along the direction D of displacement of the object. This thus generates a radiograph equivalent to a radiograph obtained by a detector, with the shape of the smallest projection of the projection plane and in which the object can be seen moving.

The improvement of the signal/noise ratio can be calculated as follows. Let x be the distance between the projection plane $P_2$ and the perpendicular $\Delta$ to the detector passing through the source 4, and let a be the width of the projection of the projection plane. For a given value of x, we have:

$$\frac{x}{FG+l} = \frac{y}{1} \text{ and } a = \frac{lx}{(FG+l)} - \frac{FGd}{FG}$$

where FGd is the distance between the source and the detector, and FG is the distance between the source and the object.

When a is smaller that the pixel size p, the values of the lines on which the projection plane is projected are used. If the displacement pitch in translation is $\Delta x$ and m successive positions are used, the combined number of pixels $N_{PS}$ to generate a resulting pixel is:

$$N_{ps} = \sum_{i=1}^{i=m}\left(\frac{l \cdot \Delta x \cdot m}{(FG+l)} \times \frac{FGd}{FG} \times \frac{1}{P} + 1\right)$$

$N_{PS}$ is significantly greater than m; consequently, the measurement statistic on the reconstructed image is always better than the statistic that would be obtained by a simple sliding total or by TDI. An estimate of this gain in the signal/noise ratio is presented below in the case of an inspection of rocket propulsion units.

According to one embodiment, the processing according to the invention can be used to build a correspondence table that associates each pixel in the radiographic image with a pixel in the projection line of a radial plane.

One embodiment could be as follows.

For the radial plane projecting orthogonally onto image N, a table Tab(k, Ie, Je)=Js is defined that associates pixel (Ie, Je) in image N+k, where k can be negative, with pixel Js in the projection of the radial plane. In this case, a radiographic image can be built up line by line in which each column is a projection of a radial plane.

Figure 3:
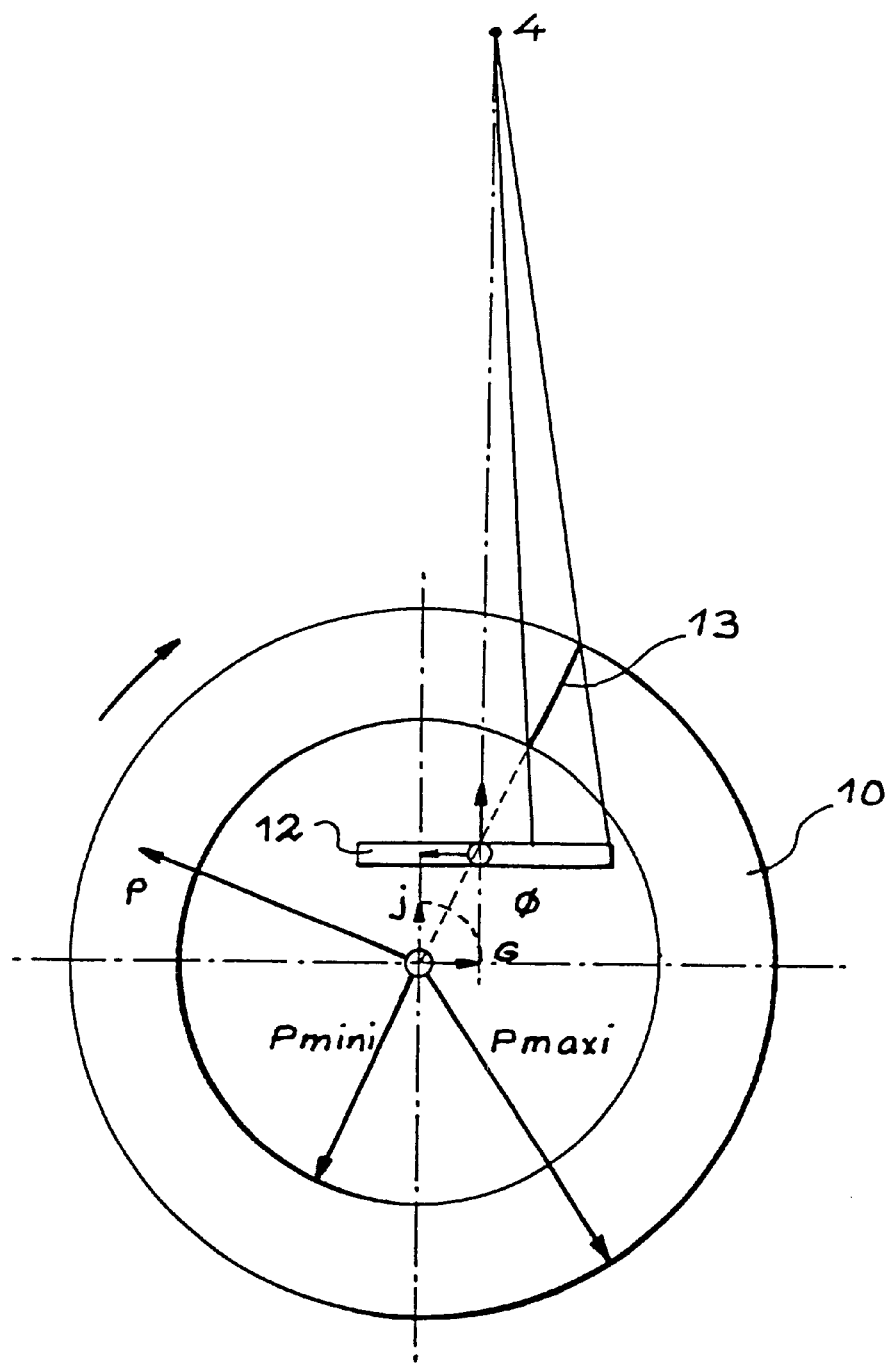
FIG. 3 is an example embodiment of the invention in the case of a mass inspection of propulsion units in radial tomography, FIG. 4 diagrammatically represents a propulsion unit ghost.

This approach has been used for the purposes of mass inspection of propulsion units (FIG. 3). For the inspection (radial radiography), unlike tangential radiography, a detector 12 is placed inside the duct of a propulsion unit 10. Therefore, the projection of the defects is displaced more quickly on the detector than in the case of tangential radiography. A diagram of the installation is shown in FIG. 3.

In the case of this application, the projection plane is a radial plane 13. The contribution of the projections from this projection plane onto the detector are summated. For example, the propulsion unit moves in the clockwise direction (direction of increasing values of φ). It could also move in the anti-clockwise direction.

The relation between the width a of the projection onto the detector and the geometry of the system is as follows:

$$a = FGd \cdot \sin\phi \left( \frac{\rho\max}{FDd - \rho\max^{\cos\phi}} - \frac{\rho\min}{FGd - \rho\min^{\cos\phi}} \right)$$

$$a \approx FGd \cdot \sin\phi \left( \frac{\rho\max}{FDd - \rho\max} - \frac{\rho\min}{FDd - \rho\min} \right)$$

where $\rho_{min}$ and $\rho_{max}$ denote the inside and outside diameters of the propulsion unit 10 respectively. As in the previous examples, 4 denotes the radiation source and FGd denotes the source-detector distance.

If it is assumed that the source is far from the detector, it can be assumed that cos φ≈1. If the objective is to guarantee a resolution better than 10 mm, in other words that the contributions of points more than 10 mm from the projection plane for which the projection is calculated are ignored, then a must be limited. If a=10 mm, $\rho_{max}$=1500 mm, $\rho_{min}$=500 mm and FGd=3000 mm, we obtain φ=0.238°.

Consequently, the processing can be done by accumulating projections while the propulsion unit is rotating over an angular sector of 2×0.238°=0.4760°, while keeping a geometric resolution better than 10 mm. Since the width of the image pixel is about 0.8 mm, each contribution corresponds to the summation of 10 lines. Secondly, there is a displacement of 0.025° between two video images, consequently accumulation will take place over 20 angular positions. Since the angles are small, the sum of the contributions will have the same contrast as the uncorrected projection, in other words of the order of $$\frac{e+l}{l}$$

with a summation of about 200 identical contributions, in other words with a signal/noise ratio improved by a factor of 14.

The performances of the TDI and of the method that we proposed were compared for a series of test ghosts with simulated and experimental data.

During experiments for a tangential radiography test, a series of measurements in radial geometry was acquired on a propulsion unit ghost in sand. This series of measures were used to make a preliminary experimental validation.

Figure 4:
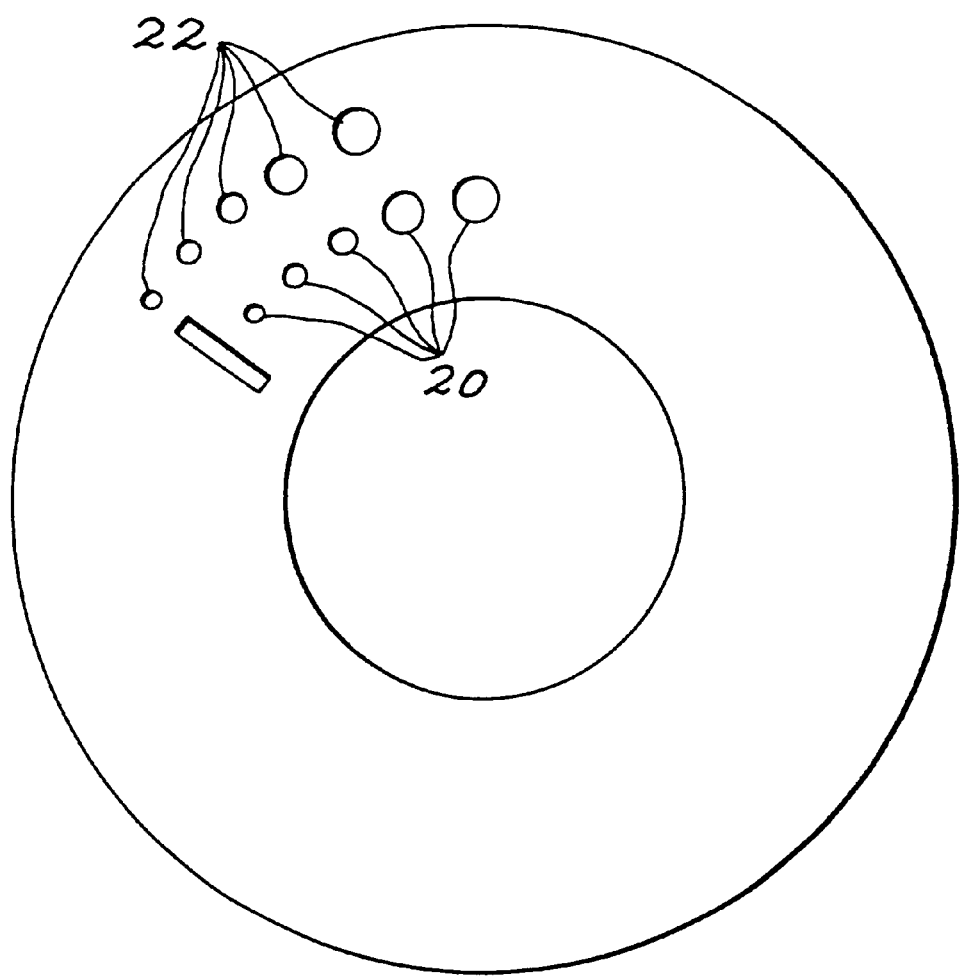

The ghost used (FIG. 4) for this acquisition is composed of two series 20, 22 of five polyethylene inserts with variable diameters. Each of the series being placed at a given ρ. The spacing between the series of inserts is 20 cm.

The distance between the source and the detector is 4 m, and the detector measures 30×40 cm; the outside diameter of the propulsion unit is 3 m and the inside diameter is 1 m. The propulsion unit rotates by 1° per second.

Figure 5A:
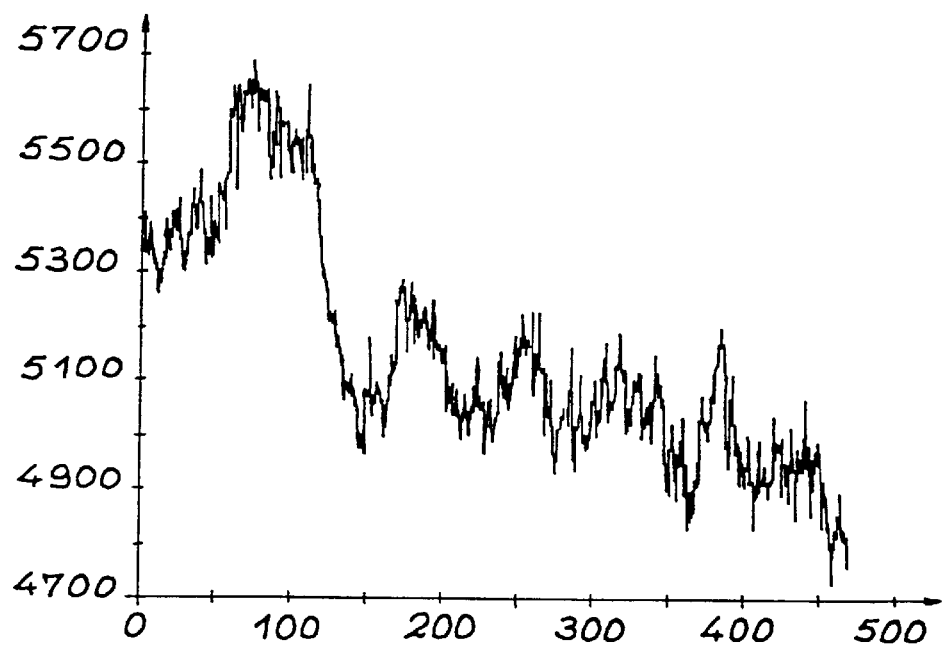
FIGS. 5A and 5B are sections of the structures in the image in TDI (on 35 radiographs), and in the radial radiography image according to the invention (on 35 successive views), respectively.

The first step was to consider that defects are initially located in the central area of the propulsion unit, and a TDI treatment was focused on this radius. The TDI was limited to the combination of 35 images. The resulting section, which depends on the structures in the TDI image on 35 radiographs is shown in FIG. 5A.

Figure 5B:
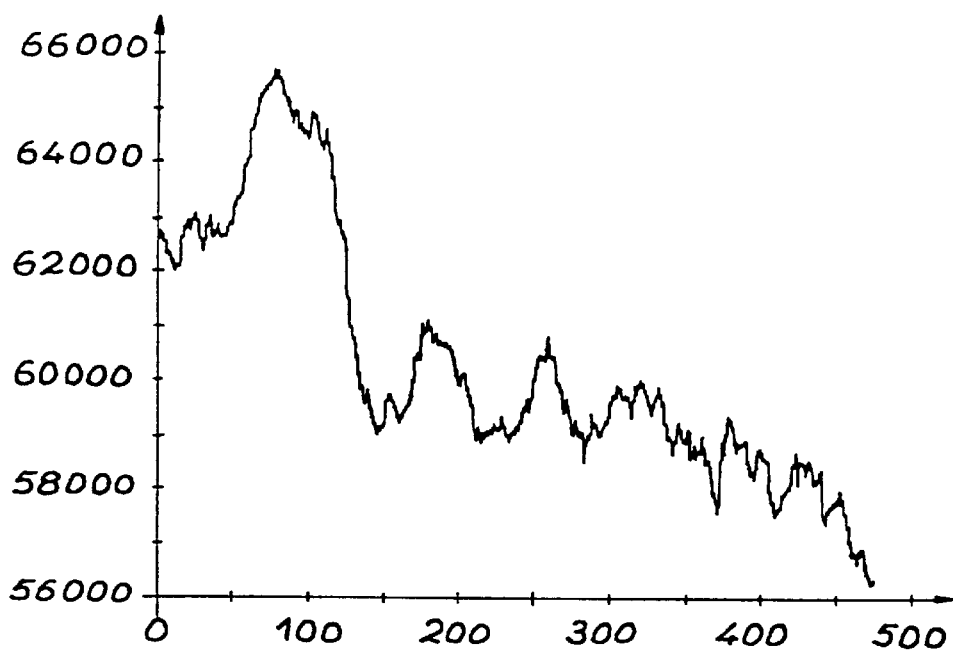

The radial radiography processing according to the invention was also carried out, by combining 35 successive images and using the radial planes as projection planes. The resulting section along the structures in the image of the radial radiograph on 35 successive views is shown in FIG. 5B.

Therefore, it can be seen that the proposed method significantly improves the signal/noise ratio, compared with the TDI method. The geometric resolution obtained with the two methods is approximately the same.

One possible radiography process for a moving object with an improved signal/noise ratio according to the invention is as follows.

Firstly, the geometry is calibrated as a function of a first series of acquisition conditions, to relate the displacement of the object to its displacement on the image. Therefore, calibration images are acquired (for example using balls or grids). This therefore gives parameters that characterize the acquisition geometry, called intrinsic parameters describing the geometry of the measurement system, and extrinsic parameters describing the trajectory of the object in the measurement coordinate system.

The next step is to define acquisition conditions specific to acquisition conditions without modifying the geometric parameters.

Correspondence tables of pixels between images can be calculated, starting from geometric parameters and acquisition conditions.

An acquisition of a series of object images can then be made.

An area of the object $S_0$ is selected, for a given position of the object. This area is projected onto the detector along a curve $C_1$; in its other positions, the projection is made according to an area $S_p$.

A projection processing along $C_1$ is then made:

a) elementary breakdown of the area $S_0$, firstly along lines 1 (called radiation attenuation lines) along which the radiation travels, from the source to the detector, and secondly along lines in a direction different to the direction of lines 1 (for example perpendicular to 1), each point on the meshed area being identified by its coordinates ($I_e$, $J_e$), b) for each position k of the object, calculate the position ($I_d$, $J_d$) in $S_p$ of the projection onto the detector of each point identified by its coordinates ($I_e$, $J_e$), the value of the measurement in ($I_d$, $J_d$) being f($I_d$, $J_d$) on $S_p$, c) calculate the projection of $S_0$ on $C_1$, which is a function of $I_d$ for all positions of the surface $S_0$ when the object is moving, starting from the different positions k of the area and definition of a function:

$$\sum_k \sum_{J_d} fk(I_d, J_d) = projIe,$$

d) move the object identifying the new position of $S_0$ in the object which is moved by one elementary position, then return to c (steps a and b are carried out once and for all), e) construction of the radiograph line by line, each line being stored.

For example for X-rays, the acquisition geometry comprises intrinsic and extrinsic parameters as follows:
  for intrinsic parameters:
    the source-detector distance,
    the sampling pitch (called the pixel size),
    the position of the projection orthogonal from the focal point of the source on the detector.
  for extrinsic parameters:
    Euler angles which define the orientation of the axis of rotation in the source-detector coordinate system,
    the position of the origin and the center line in the source-detector coordinate system.

Acquisition conditions are as follows:
the object displacement speed and its position (for example the radius in the case of a circular geometry; or curvilinear abscissa on an arbitrary trajectory). A construction of the trajectory of the object can be deduced in the source-detector coordinate system;
the trajectory,
the acquisition frequency
the image size.

For example for infrared rays, the camera is the radiation source and the trajectory of the object in the camera coordinate system is found.

All data processing described above in this application may be carried out by a computer programmed specifically for this purpose. Appropriate program instructions may be stored on magnetic disks or in conventional RAM or ROM units.

What is claimed is:

1. Radiography process for use with a moving object between a source and a detector, comprising:
    determining a plane, called the object projection plane, such that the radiographic image of this plane is a line, for one of the positions of the moving object,
    producing radiographic images of the object while it is moving, using the source and the detector (6), and
    combining the various contributions of projections of the projection plane in the series of radiographic images obtained.

2. Process according to claim 1, the combination step being a step in which the values corresponding to the projection of the projection plane are summated.

3. Process according to claim 2, the object moving in translation along a direction (D) and having a thickness l along the direction of the projection plane, the number of combined pixels to generate one pixel in the resulting image being equal to:

$$N_{ps} = \sum_{i=1}^{i=m}\left(\frac{l \cdot \Delta x \cdot m}{(FG+l)} \times \frac{FGd}{FG} \times \frac{1}{P} + 1\right)$$

where p is the size of a pixel, and where FG and FGd represent the distance between the source and the object and the distance between the source and the detector respectively, and where m is the number of successive positions of the object separated by a distance Δx for which an image is created.

4. Process according to claim 1, the movement of the object being circular, and the projection plane being a radial plane of the object.

5. Process according to claim 1, a correspondence table being built, which associates each pixel in the projection line of the projection plane.

6. Process according to claim 5, in which a table Tab(k, $I_e$, $J_e$)=Js is defined which associates pixel ($I_e$, $J_e$) in image N+k, where k is a positive or negative integer, with pixel Js in the projection of the projection plane.

7. Radiography process applicable for an object moving between a source and a detector, comprising:
    determining a first area $S_0$ for a given position of the object, this first area being projected onto the detector along a curve ($C_1$), its projection taking place based on a second area $S_p$ in its other positions,
    producing radiographic images of the object as it moves, using the source and the detector,
    processing the projection along said curve ($C_1$) comprising the following steps:
    a) breaking down the first area $S_0$, firstly along lines along the direction of the radiation from the source to the detector, called radiation attenuation lines, and secondly along lines in a direction different from the directions of the radiation attenuation lines, each point on the meshed area being identified by its coordinates ($I_e$, $J_e$),
    b) for each position k of the object, calculate the position ($I_d$, $J_d$), in the second area $S_p$, of the projection onto the detector of each point identified by its coordinates ($I_e$, $J_e$), the value of the measurement in ($I_d$, $J_d$) being f($I_d$, $J_d$) on the second area $S_p$,
    c) calculating the projection of the first area $S_0$ on the curve which is a function of $I_d$, for all positions of the first area $S_0$ while the object is moving, starting from the different positions k of the first area, and defining a function:

$$\sum_k \sum_{J_d} fk(I_d, J_d) = projle$$

d) as the object moves, identifying the new position of the first area $S_0$ in the object which had moved by one elementary position, then return to step c),
    e) constructing the radiograph line by line with each line being stored.

8. Process according to claim 7, also comprising a step in which the geometry is calibrated as a function of a first series of acquisition conditions, to relate the movement of the object to its displacement on the image, and to obtain the characteristic parameters of the acquisition geometry called the intrinsic parameters describing the geometry of the measurement system, and extrinsic parameters describing the geometry of the measurement system and extrinsic parameters describing the trajectory of the object in the measurement coordinate system.

9. Process according to claim 7, also comprising a step in which the acquisition conditions are defined specific to the acquisition conditions without modification of the geometric parameters.

10. Process according to claim 2, the movement of the object being circular, and the projection plane being a radial plane of the object.

11. Process according to claim 2, a correspondence table being built, which associates each pixel in the projection line of the projection plane.

12. Process according to claim 8, also comprising a step in which the acquisition conditions are defined specific to the acquisition conditions without modification of the geometric parameters.

* * * * *